United States Patent
Bratton et al.

(10) Patent No.: US 10,984,076 B1
(45) Date of Patent: Apr. 20, 2021

(54) IMMUNIZATION WEB PORTAL

(71) Applicant: WALGREEN CO., Deerfield, IL (US)

(72) Inventors: Edward J. Bratton, Gurnee, IL (US); Nicholas J. Leners, Round Lake, IL (US)

(73) Assignee: WALGREEN CO., Deerfield, IL (US)

( * ) Notice: Subject to any disclaimer, the term of this patent is extended or adjusted under 35 U.S.C. 154(b) by 532 days.

(21) Appl. No.: 15/041,389

(22) Filed: Feb. 11, 2016

(51) Int. Cl.
*G16H 50/30* (2018.01)
*G16H 15/00* (2018.01)
*G16H 10/60* (2018.01)
*G06F 19/00* (2018.01)

(52) U.S. Cl.
CPC ........ *G06F 19/3481* (2013.01); *G06F 19/325* (2013.01); *G16H 10/60* (2018.01); *G16H 15/00* (2018.01); *G16H 50/30* (2018.01)

(58) Field of Classification Search
CPC ........ G16H 10/00; G16H 10/60; G16H 15/00; G16H 20/10; G16H 50/50; G16H 10/65; G16H 50/70; G16H 50/20
See application file for complete search history.

(56) References Cited

U.S. PATENT DOCUMENTS

| | | | | |
|---|---|---|---|---|
| 5,758,095 A | * | 5/1998 | Albaum ................ | G06F 19/326 705/2 |
| 2003/0097279 A1 | * | 5/2003 | delusignan .......... | G06F 19/3481 705/2 |
| 2006/0218010 A1 | * | 9/2006 | Michon ................ | G06F 19/3456 705/3 |
| 2008/0091471 A1 | * | 4/2008 | Michon ................. | G06Q 40/08 705/3 |
| 2011/0029488 A1 | * | 2/2011 | Fuerst ................ | G06F 19/3418 707/636 |
| 2012/0179481 A1 | * | 7/2012 | Patel ..................... | G06Q 30/02 705/2 |
| 2016/0034650 A1 | * | 2/2016 | DeLoach .............. | G06F 19/328 705/2 |

OTHER PUBLICATIONS

Charles Phelps et al., "A priority-setting aid for new vaccine candidates", Mar. 4, 2014, Proceedings of the National Academy of Sciences CrossMark, vol. 111, No. 9, pp. 3199-3200 (See, www.pnas.org/content/111/9/3199).*
Amy Metroka et al., "Defining Functional Requirements for Immunization Information Systems", copyrigh 2012, Public Health Informatics Institute; pp. 1-124.*

* cited by examiner

*Primary Examiner* — Hiep V Nguyen
(74) *Attorney, Agent, or Firm* — Marshall, Gerstein & Borun LLP; Randall G. Rueth

(57) ABSTRACT

An immunization web portal may identify whether a patient is eligible to receive vaccines for a specified vaccine-preventable disease. The patient's eligibility may be identified by comparing biographical data and medical characteristics for the patient to a set of eligibility requirements according to state and federal law. If the patient is eligible, the immunization web portal may display indications of several vaccines corresponding to the vaccine-preventable disease, and a user such as a pharmacist or technician may select one of the vaccines so that the selected vaccine may be administered to the patient.

18 Claims, 8 Drawing Sheets

300

| | | |
|---|---|---|
| 302 — | Which vaccine are you looking to receive? | Select One: ▼  ?  — 314 |
| 304 — | Do you have a prescription from your prescriber? | ○ Yes  ○ No — 316 |
| 306 — | Select Gender | ○ Male  ○ Female — 318 |
| 308 — | What is your birthday date? | [____] — 320 |
| 310 — | Have you had a severe reaction to any vaccine previously? | ○ Yes  ○ No — 322 |
| 312 — | Is there any chance that you may be pregnant? | ○ Yes  ○ No — 324 |

Submit — 326

*FIG. 2A*

| State/Federal | Disease | Eligibility Requirements | Allows High Risk? | High Risk Criteria |
|---|---|---|---|---|
| Michigan | Hepatitis A | • Ages 3-4<br>• Contraindications: allergic reaction to a prior dose or components | No | |
| Illinois | Hepatitis A | • Ages 1-2<br>• Contraindications: allergic reaction to a prior dose or components | Yes | • Injection drug users<br>• Chronic liver disease<br>• People working with HAV infected primates |
| Illinois | Pneumonia | • Ages 0-5<br>• Ages : 65+<br>• Contraindications: allergic reaction to a prior dose or components | Yes | • Sickle cell disease<br>• HIV<br>• Lymphoma<br>• Hodgkin disease<br>• Organ transplant<br>• Cirrhosis<br>• Diabetes |
| Federal | Pneumonia | • Ages 0-5<br>• Ages 65+<br>• Contraindications: allergic reaction to a prior dose or components | Yes | • Sickle cell disease<br>• HIV<br>• Lymphoma<br>• Hodgkin disease<br>• Organ transplant |
| Wisconsin | Influenza | • Ages 6 months+ | No | |

First*: [ ] Middle: [ ] Last*: [ ] Suffix: [ ▼ ]

[ ] No Known Health Condition  [ ] Health Condition(s) Not Listed

<u>Eligible Health Conditions</u>

402
[ ] A damaged spleen/No spleen
[ ] Alcoholism
[ ] Asthma on High Dose Steroids
[ ] Brain or Spinal Cord Fluid Leaks
[ ] Cardiac Failure
[ ] Chemotherapy
[ ] Chronic Kidney Failure
[ ] Chronic Liver Disease
[ ] Chronic Lung Disease

[ ] Cochlear Implants
[ ] Congenital Heart Disease
[ ] Diabetes
[ ] Hemoglobin Disorder
[ ] HIV Infection
[ ] Hodgkin Disease — 406
[ ] Immune System disorder
[ ] Immunosuppression Therapy
[ ] Kidney Disease 404
[ ] Kidney Disease
[ ] Leukemias
[ ] Lymphomas
[ ] Malignant Cancer
[ ] Multiple Myeloma
[ ] Radiation Therapy
[ ] Sickle Cell Disease — 408
[ ] Solid Organ Transplant

* - required fields

[ Submit ] — 410

FIG. 2C

| | | |
|---|---|---|
| ☑ | FLUVIRIN MDV TIV 2015-16 .5ML | 66521-0118-10 Preferred |
| ☐ | FLUVIRIN PFS TIV 2015-16 INJ, 0.5ML | 66521-0118-02 |
| ☐ | FLUMIST QUAD NASAL SUSP 2015-2016 | 66019-0302-10 |
| ☐ | FLUZONE MDV TIV 2015-16 INJ, 0.5ML | 49281-0396-15 |
| ☐ | FLUARIX PFS QUAD 2015-2016 INJ, 0.5ML | 58160-0903-52 |

*FIG. 2D*

**Based on the entered information, this vaccine *cannot* be administered**

Cannot be administered to a patient of this age in your state     ZOSTA VAX INJ SINGLE DOSE VIAL 10PK    00006-4963-41

*FIG. 2E*

PATIENT INFORMATION (ALL FIELDS ARE REQUIRED)

| Name: John Doe | | Date: 08/17/2015 |
|---|---|---|
| Date of Birth: 08/11/1950 | Age from IC+: 65 | Phone: |
| Address: | | |

| ProductName: | NDC | IC+ Qty | Directions |
|---|---|---|---|
| FLUVIRIN MDV TIV 2015-16 5 ML | 66521-0118-10 | 1.000 | Shake vigorously and administer 0.5 ml |

PROTOCOL PRESCRIBER/ADMINISTERING PHARMACIST INFORMATION (ALL FIELDS ARE REQUIRED)

| Name: Dr.Smith | DEA/NPI: 5555555555 | Phone: (555) 123-4567 |
|---|---|---|

*FIG. 2F*

IMMUNIZATION WEB PORTAL

TECHNICAL FIELD

The present disclosure generally relates to a system and method for identifying vaccines to be administered to a patient and, more particularly to determining whether the patient is eligible to receive vaccines corresponding to a vaccine-preventable disease and causing one of the vaccines to be administered to the patient.

BACKGROUND

Today, health care providers assess eligibility for administering vaccines based on a patient's answers to several questions. In some situations, the health care provider may consult a chart which provides eligibility criteria.

However, these methods can be inaccurate in that health care providers may not be aware of specific state regulations for assessing eligibility or may not consider certain factors which make the vaccination dangerous for the patient. According to *Vaccination Errors Reported to the Vaccine Adverse Event Reporting System*, (*VAERS*) United States, 2000-2013,[1] vaccination-related errors grew from 10 in the year 2000 to 4,324 in 2013. One of the most common errors was dispensing vaccines at an inappropriate schedule (vaccination schedules specify the timing of all doses), and one-quarter of reported errors caused an adverse health effect.

[1] Hibbs et al., *Vaccination Errors Reported to the Vaccine Adverse Event Reporting System*, (*VAERS*) United States, 2000-2013, Vaccine, vol. 32, issue 28, pp. 3171-78 (June 2015).

SUMMARY

To identify vaccines which may be administered to a patient, a vaccine administration system may receive a request from a patient to receive a vaccine corresponding to a specified vaccine-preventable disease, such as influenza, pneumococcal disease, cholera, diphtheria, hepatitis A, hepatitis B, meningitis, measles, mumps, pertussis, polio, rubella, tetanus, tuberculosis, yellow fever, typhoid fever, human papilloma-virus, etc. In response to the request, the vaccine administration system may retrieve a set of eligibility requirements for vaccines which prevent the disease.

The eligibility requirements may be based on federal and state law. For example, for a patient who requests a Hepatitis A vaccine in Illinois, the vaccine administration system may retrieve a set of eligibility requirements for Hepatitis A vaccines according to federal and Illinois law. The eligibility requirements may include a recommended age range for receiving the vaccine and a high risk age range for patients who fall outside of the recommended age range but have certain medical conditions that put them at a high risk of contracting, being infected with, or suffering complications from the vaccine-preventable disease. The eligibility requirements may also include contraindications which may cause the patient to become ineligible to receive vaccines for the vaccine-preventable disease due to the potential harm to the patient. For example, contraindications may include pregnancy, a weakened immune system, a previous allergic reaction to the vaccine, kidney disease, heart disease, lung disease, etc.

The vaccine administration system may also retrieve patient biographical data for the patient to determine whether the patient meets the eligibility requirements. In some embodiments, a patient information retrieval screen may provide a list of questions to ask the patient. Additionally, the patient biographical data may be retrieved from a patient profile which stores the patient's name, date of birth, medical characteristics, etc. When the patient meets the eligibility requirements, several vaccines corresponding to the vaccine-preventable disease may be displayed. In some embodiments, the vaccines may be displayed in a ranked order according to their clinical results. When a user such as a pharmacist selects one of the vaccines, the vaccine administration system may generate a vaccination standing order for a health care provider to administer the selected vaccine to the patient.

In this manner, the vaccine administration system may accurately determine whether the patient is eligible to receive vaccines for a specified vaccine-preventable disease. Additionally, when the patient is eligible the vaccination administration system may prioritize vaccines for the patient (e.g., according to clinical results). The present embodiments advantageously ensure that vaccines are administered to eligible patients, reducing the likelihood that the patients experience adverse health effects and increasing the likelihood that eligible patients are properly vaccinated immunizing them from deadly diseases.

Additionally, by prioritizing vaccines, the vaccination administration system advantageously identifies the most effective vaccine at preventing the specified vaccine-preventable disease based on the patient's biographical data and medical characteristics. As a result, patients are less likely to suffer undesirable side effects or other complications from receiving vaccines. Furthermore, the present embodiments advantageously evaluate eligibility according to state law and pharmacy qualifications, further increasing the accuracy in which eligibility is evaluated.

In one embodiment, a computer-implemented method for identifying vaccines to be administered to a patient includes receiving a request for a vaccine for preventing a specified disease to be administered to a patient, obtaining patient biographical data for the patient, determining a set of eligibility requirements for the patient to receive vaccines for preventing the specified disease according to federal and state law based on a location of the patient, and determining whether the patient meets the set of eligibility requirements by comparing the set of patient eligibility requirements to the patient biographical data. When the patient meets the set of eligibility requirements, the method includes identifying a plurality of vaccines for preventing the specified disease that the patient is eligible to receive based on the patient biographical data. The method further includes causing indications of the plurality of vaccines to be displayed on a user interface for administering one of the plurality of vaccines to the patient, and for a selected vaccine of the plurality of vaccines, causing a vaccination standing order to be pre-populated for the patient, wherein the pre-populated vaccination standing order is provided to a health care provider so as to cause the selected vaccine to be administered to the patient.

In another embodiment, a system for identifying vaccines to be administered to a patient is provided. The system includes one or more processors, a communication network and a non-transitory computer-readable memory coupled to the one or more processors, and the communication network and storing instructions thereon. When executed by the one or more processors, the instructions cause the system to receive, via the communication network, a request for a vaccine for preventing a specified disease to be administered to a patient, obtain patient biographical data for the patient, identify a set of eligibility requirements for the patient to receive vaccines for preventing the specified disease according to federal and state law based on a location of the patient, and determine whether the patient meets the set of eligibility requirements by comparing the set of patient eligibility requirements to the patient biographical data. When the patient meets the set of eligibility requirements, the instructions cause the system to identify a plurality of vaccines for preventing the specified disease that the patient is eligible to receive based on the patient biographical data. The instructions further cause the system to cause, via the communication network, indications of the plurality of vaccines to be displayed on a user interface for administering one of the plurality of vaccines to the patient, and for a selected vaccine of the plurality of vaccines, cause a vaccination standing order to be pre-populated for the patient, wherein the pre-populated vaccination standing order is provided to a health care provider so as to cause the selected vaccine to be administered to the patient.

BRIEF DESCRIPTION OF THE DRAWINGS

The figures described below depict various aspects of the system and methods disclosed therein. It should be understood that each figure depicts an embodiment of a particular aspect of the disclosed system and methods, and that each of the figures is intended to accord with a possible embodiment thereof. Further, wherever possible, the following description refers to the reference numerals included in the following figures, in which features depicted in multiple figures are designated with consistent reference numerals.

FIG. 2A illustrates an exemplary patient information retrieval screen in accordance with the presently described embodiments;

FIG. 2B illustrates an exemplary eligibility data table in accordance with the presently described embodiments;

FIG. 2C illustrates an exemplary additional health risk information retrieval screen in accordance with the presently described embodiments;

FIG. 2D illustrates an exemplary vaccination screen in accordance with the presently described embodiments;

FIG. 2E illustrates an exemplary ineligible vaccination screen when the patient is ineligible to receive a vaccination in accordance with the presently described embodiments;

FIG. 2F illustrates an exemplary vaccination standing order screen in accordance with the presently described embodiments.

DETAILED DESCRIPTION

Figure 1A:
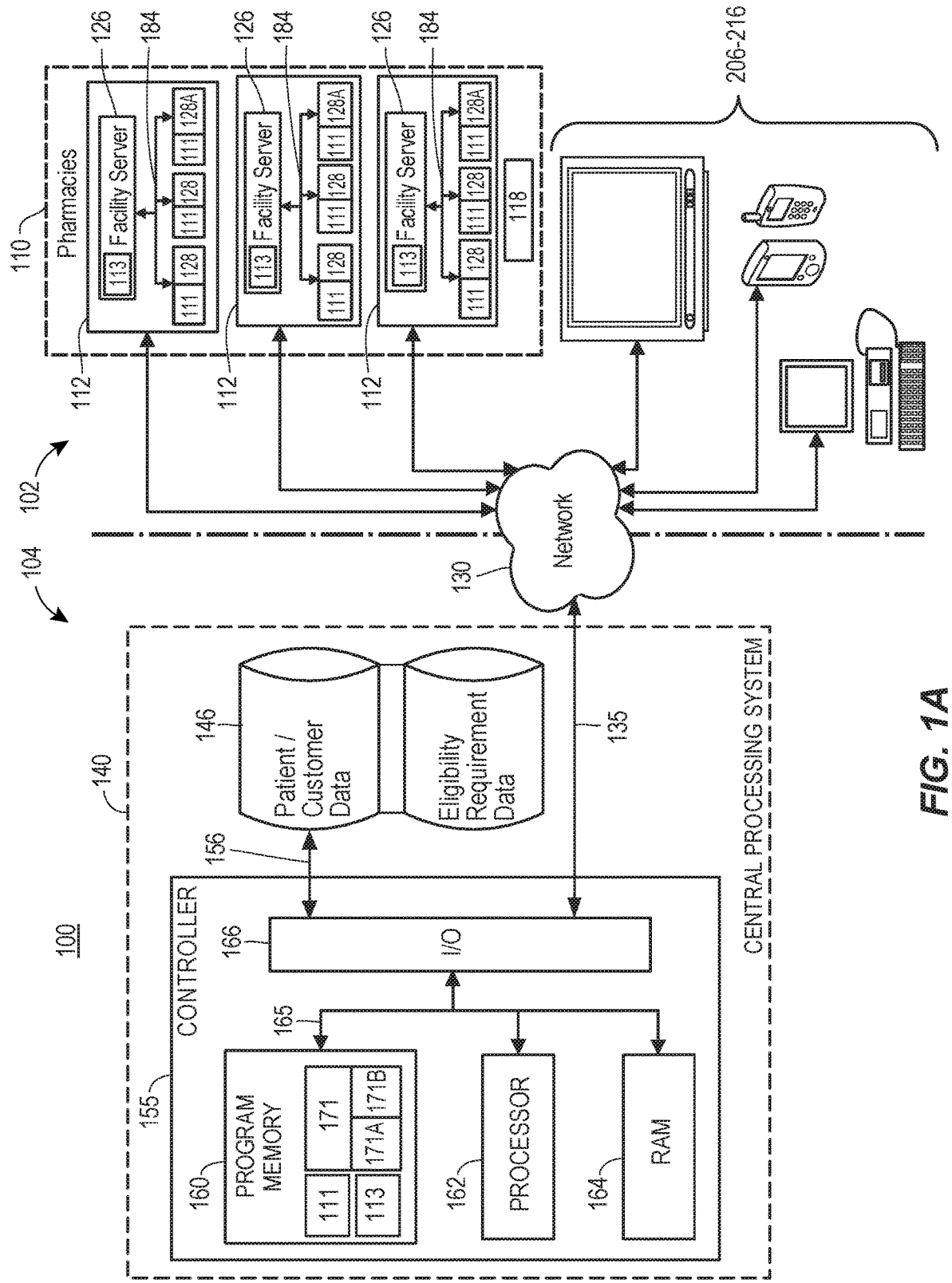
FIG. 1A illustrates a block diagram of a computer network and system on which an exemplary vaccine administration system and method may operate in accordance with the described embodiments.

Although the following text sets forth a detailed description of numerous different embodiments, it should be understood that the legal scope of the description is defined by the words of the claims set forth at the end of this patent and equivalents. The detailed description is to be construed as exemplary only and does not describe every possible embodiment since describing every possible embodiment would be impractical. Numerous alternative embodiments could be implemented, using either current technology or technology developed after the filing date of this patent, which would still fall within the scope of the claims.

It should also be understood that, unless a term is expressly defined in this patent using the sentence "As used herein, the term '_____' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. § 112, sixth paragraph.

Generally speaking, techniques for identifying vaccines to be administered to a patient may be implemented in a client computing device, one or several network servers or a system that includes a combination of these devices. However, for clarity, the examples below focus primarily on an embodiment in which a pharmacy workstation, such as a desktop computer, obtains a request to receive a vaccine corresponding to a specified vaccine-preventable disease. The pharmacy workstation may display several questions for the patient regarding eligibility to receive the vaccine as well as user controls for obtaining answers from the patient. The pharmacy workstation may then transmit the request and answers to the eligibility questions to a central processing system (which may include one or several network servers), which in turn may compare the patient's answers to a set of eligibility requirements for receiving vaccines to prevent the specified disease. Based on the comparison, the central processing system may generate indications of several vaccines corresponding to the specified vaccine-preventable disease that the patient is eligible to receive. The indications may be transmitted to the pharmacy workstation for display. In other embodiments, the pharmacy workstation may transmit the request to a facility server which may generate indications of several vaccines that the patient is eligible to receive. In yet other embodiments, a web-enabled device such as a smart-phone or tablet computer may display questions for the patient regarding eligibility to receive the vaccine and user controls for obtaining answers.

FIG. 1A illustrates various aspects of an exemplary architecture implementing a vaccine administration system 100. The high-level architecture includes both hardware and software applications, as well as various data communications channels for communicating data between the various hardware and software components. The vaccine administration system 100 may be roughly divided into front-end components 102 and back-end components 104. The front-end components 102 are primarily disposed within a retail network 110 including one or more pharmacies 112. The pharmacies 112 may be located, by way of example rather than limitation, in separate geographic locations from each other, including different areas of the same city, different cities, or even different states. The front-end components 102 comprise a number of pharmacy workstations 128. The pharmacy workstations 128 are local computers located in the various pharmacies 112 throughout the retail network 110 and executing various pharmacy management-related applications. Pharmacists, technicians, and other pharmacy personnel, referred to collectively herein simply as "pharmacists" (not shown), use the pharmacy workstations 128 to access customer information, select a vaccine to be administered to a patient, generate a vaccination standing order and so forth. Each of the pharmacies 112 may be, for example, an in-store retail pharmacy, an on-line pharmacy, a mail-order pharmacy, a long-term care pharmacy, a workplace/on-site pharmacy, or a specialty pharmacy. The retail network 110 may also include one or more warehouses or central-filling facilities 118. The warehouses or central-filling facilities 118 may distribute medications or retail products to the various retail pharmacies 112 in the retail network 110, or may distribute medications or retail products directly to customers.

In some embodiments, pharmacists may also use web-enabled devices 206-216 to interact with the vaccine administration system 100. The web-enabled devices 206-216 may be communicatively connected to the pharmacies 112 and to a system 140 through a digital network 130, as described below. The web-enabled devices 206-216 may include, by way of example, a tablet computer, a web-enabled cell phone, a personal digital assistant (PDA), a mobile device smart-phone also referred to herein as a "mobile device," a laptop computer, a desktop computer, a portable media player (not shown), a wearable computing device such as Google Glass™ (not shown), etc. Of course, any web-enabled device appropriately configured may interact with the vaccine administration system 100. The web-enabled devices 206-216 need not necessarily communicate with the network 130 via a wired connection. In some instances, the web-enabled devices 206-216 may communicate with the network 130 via wireless signals and, in some instances, may communicate with the network 130 via an intervening wireless or wired device which may be a wireless router, a wireless repeater, a base transceiver station of a mobile telephony provider, etc. Each of the web-enabled devices 206-216 may interact with the central processing system 140 to receive web pages, application views or server data from the central processing system 140 and may display the web pages, application views or server data via a client application (described below). For example, web-enabled devices 206-216 may display the client application to a user, may receive an input from the user, and may interact with the central processing system 140 depending on the type of user-specified input.

Those of ordinary skill in the art will recognize that the front-end components 102 could also comprise a plurality of facility servers 126 disposed at the plurality of pharmacies 112 instead of, or in addition to, a plurality of pharmacy workstations 128. Each of the pharmacies 112 may include one or more facility servers 126 that may facilitate communications between the workstations 128 or client device terminals 128A of the pharmacies 112 via a digital network 130, and may store information for a plurality of customers/employees/accounts/etc. associated with each facility. Of course, a local digital network 184 may also operatively connect each of the workstations 128 to the facility server 126. Unless otherwise indicated, any discussion of the workstations 128 also refers to the facility servers 126, and vice versa. Moreover, environments other than the pharmacies 112 may employ the workstations 128 and the servers 126. As used herein, the term "pharmacy" refers to any of these environments (e.g., call centers, kiosks, Internet interface terminals, etc.) in addition to the retail pharmacies 112, etc. described above.

The front-end components 102 communicate with the back-end components 104 via the digital network 130. One or more of the front-end components 102 may be excluded from communication with the back-end components 104 by configuration or by limiting access due to security concerns. For example, the web-enabled devices 206-216 may be excluded from direct access to the back-end components 104. In some embodiments, the pharmacies 112 may communicate with the back-end components via the digital network 130. In other embodiments, the pharmacies 112 and web-enabled devices 206-216 may communicate with the back-end components 104 via the same digital network 130, but digital access rights, IP masking, and other network configurations may deny access to the web-enabled devices 206-216.

The digital network 130 may be a proprietary network, a secure public Internet, a virtual private network or some other type of network, such as dedicated access lines, plain ordinary telephone lines, satellite links, combinations of these, etc. Where the digital network 130 comprises the Internet, data communication may take place over the digital network 130 via an Internet communication protocol. The back-end components 104 include the central processing system 140 (also referred to herein as a "server") within a central processing facility, such as, for example, the central processing facility described in U.S. Pat. No. 8,175,891 entitled "DISTRIBUTED PHARMACY PRESCRIPTION PROCESSING SYSTEM" the entire disclosure of which is incorporated by reference herein. Of course, the pharmacies 112 may be communicatively connected to different back-end components 104 having one or more functions or capabilities that are similar to the central processing system 140. The central processing system 140 may include one or more computer processors 162 adapted and configured to execute various software applications and components of the vaccine administration system 100, in addition to other software applications. The central processing system 140 further includes a database 146. The database 146 is adapted to store data related to the operation of the vaccine administration system 100 (e.g., patient profile data including patient name, gender, date of birth, and medical characteristics as well as eligibility requirement data for vaccines to prevent each disease including federal eligibility requirements, eligibility requirements for each state, whether each state allows high risk patients to receive vaccines, medical conditions to qualify as a high risk patient for a specified disease, etc.). The central processing system 140 may access data stored in the database 146 when executing various functions and tasks associated with the operation of the vaccine administration system 100.

Although FIG. 1A depicts the vaccine administration system 100 as including the central processing system 140 in communication with three pharmacies 112, and various web-enabled devices 206-216 it should be understood that different numbers of processing systems, pharmacies, and devices may be utilized. For example, the digital network 130 (or other digital networks, not shown) may interconnect the central processing system 140 to a plurality of included central processing systems 140, hundreds of pharmacies 112, and thousands of web-enabled devices 206-216. According to the disclosed example, this configuration may provide several advantages, such as, for example, enabling near real-time uploads and downloads of information as well as periodic uploads and downloads of information. This provides for a primary backup of all the information generated in the new prescription process. Alternatively, some of the pharmacies 112 may store data locally on the facility server 126 and/or the workstations 128.

FIG. 1A also depicts one possible embodiment of the central processing system 140. The central processing system 140 may have a controller 155 operatively connected to the database 146 via a link 156 connected to an input/output (I/O) circuit 166. It should be noted that, while not shown, additional databases may be linked to the controller 155 in a known manner.

The controller 155 includes a program memory 160, the processor 162 (may be called a microcontroller or a microprocessor), a random-access memory (RAM) 164, and the input/output (I/O) circuit 166, all of which are interconnected via an address/data bus 165. It should be appreciated that although only one microprocessor 162 is shown, the controller 155 may include multiple microprocessors 162. Similarly, the memory of the controller 155 may include multiple RAMs 164 and multiple program memories 160. Although the I/O circuit 166 is shown as a single block, it should be appreciated that the I/O circuit 166 may include a number of different types of I/O circuits. The RAM(s) 164 and the program memories 160 may be implemented as semiconductor memories, magnetically readable memories, and/or optically readable memories, for example. A link 135 may operatively connect the controller 155 to the digital network 130 through the I/O circuit 166.

The program memory 160 may also contain machine-readable instructions (i.e., software) 171, for execution by the processor 162. The software 171 may perform the various tasks associated with operation of the pharmacy or pharmacies, and may be a single module 171 or a plurality of modules 171A, 171B. While the software 171 is depicted in FIG. 1A as including two modules, 171A and 171B, the software 171 may include any number of modules accomplishing tasks related to pharmacy operation including, for example, receiving patient biographical data, identifying vaccines which the patient is eligible to receive, etc. The central processing system 140 implements a server application 113 for providing data to a user interface application 111 operating on the workstations 128.

Figure 1B:
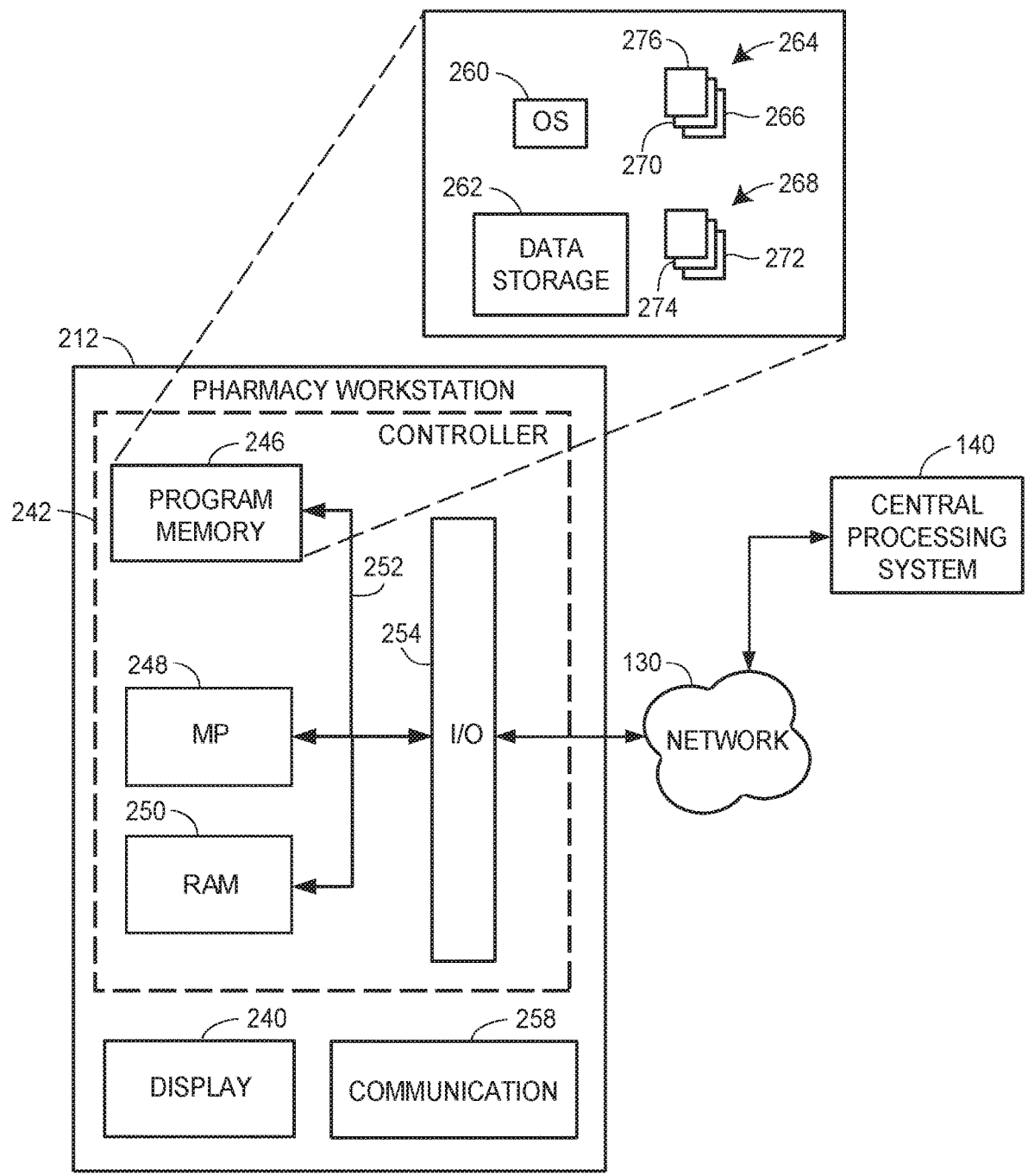
FIG. 1B illustrates pharmacy workstations and associated equipment that may operate with a network and a server.

For purposes of implementing the vaccine administration system 100, a user interacts with the pharmacy systems (e.g., the central processing system 140) via the pharmacy workstation 128, a web-enabled device 206-216 (e.g., mobile device application, etc.), a specialized application, or a plurality of web pages. Each of the pharmacy workstations 128 and/or web-enabled devices 206-216 may interact with the central processing system 140 to receive web pages, application views or server data from the central processing system 140 and may display the web pages, application views or server data via a client application (described below). FIG. 1B depicts the pharmacy workstation 128 connected via the network 130 to the central processing system 140 through which a user may initiate and interact with the vaccine administration system 100 (as shown in FIG. 1A). Although the following description addresses the design of the pharmacies 112, it should be understood that the design of one or more of the pharmacies 112 may be different from the design of others of the pharmacies 112. Also, each of the pharmacies 112 may have various different structures and methods of operations. It should also be understood that while the embodiments shown in FIG. 1B illustrates some of the components and data connections that may be present in a pharmacy 112, it does not illustrate all of the data connections that may be present in a pharmacy 112. For exemplary purposes, one design of a pharmacy is described below, but it should be understood that numerous other designs may be utilized.

The pharmacy workstation 128 includes a display 240, a communication unit 258, a user-input device (not shown), and, like the central processing system, a controller 242. Similar to the controllers 155, the controller 242 includes a program memory 246, one or more microcontrollers or microprocessors (MP) 248, a random-access memory (RAM) 250, and an input/output (I/O) circuit 254, all of which are interconnected via an address/data bus 252. The program memory 246 includes an operating system 260, a data storage 262, a plurality of software applications 264, and a plurality of software routines 268. The operating system 260, for example, may include Microsoft Windows®, OS X®, Linux®, Unix®, etc. The data storage 262 may include data such as user profiles, application data for the plurality of applications 264, routine data for the plurality of routines 268, and other data necessary to interact with the central processing system 140, the facility servers 126, or the server applications 113 through the digital network 130. In some embodiments, the controller 242 may also include, or otherwise be communicatively connected to, other data storage mechanisms (e.g., one or more hard disk drives, optical storage drives, solid state storage devices, etc.) that reside within the pharmacy workstation 128.

The communication unit 258 may communicate with the central processing system 140 or the facility servers 126 via any suitable wireless communication protocol network, such as a wireless telephony network (e.g., GSM, CDMA, LTE, etc.), a Wi-Fi network (802.11 standards), a WiMAX network, a Bluetooth network, etc.

The user-input device (not shown) may include an external hardware keyboard communicating via a wired or a wireless connection (e.g., a Bluetooth keyboard), an external mouse, a touch screen or any other suitable user-input device. As discussed with reference to the controllers 155, it should be appreciated that although FIG. 1B depicts only one microprocessor 248, the controller 242 may include multiple microprocessors 248. Similarly, the memory of the controller 242 may include multiple RAMs 250 and multiple program memories 246. Although FIG. 1B depicts the I/O circuit 254 as a single block, the I/O circuit 254 may include a number of different types of I/O circuits. The controller 242 may implement the RAM(s) 250 and the program memories 246 as semiconductor memories, magnetically readable memories, and/or optically readable memories, for example.

The one or more processors 248 may be adapted and configured to execute any one or more of the plurality of software applications 264 and/or any one or more of the plurality of software routines 268 residing in the program memory 242, in addition to other software applications. One of the plurality of applications 264 may be a client application 266 that may be implemented as a series of machine-readable instructions for performing the various tasks associated with receiving information at, displaying information on, and transmitting information from the pharmacy workstation. One of the plurality of applications 264 may be a native application or web browser 270, such as Apple's Safari®, Google Chrome™, Microsoft Internet Explorer®, and Mozilla Firefox® that may be implemented as a series of machine-readable instructions for receiving, interpreting, and displaying web page information or application data from the central processing system 140, the facility servers 126, or the server applications 113 while also receiving inputs from the user. Another application of the plurality of applications may include an embedded web browser 276 that may be implemented as a series of machine-readable instructions for receiving, interpreting, and displaying web page information from the central processing system 140, facility servers 126, or server applications 113 within the client application 266.

One of the plurality of routines may include a patient eligibility determination routine 272 that coordinates with the display 240 to retrieve user input and determine whether the patient is eligible to receive vaccines corresponding to a specified vaccine-preventable disease. The patient eligibility determination routine 272 may be for use with one or more of the plurality of applications, such as the client application 266, or for use with other routines. Another routine in the plurality of routines may include a vaccine selection routine 274 that displays several vaccines which the patient is eligible to receive and in response to selection input for one of the vaccines, generates a vaccination standing order for a health care provider to administer the vaccine. Likewise, the vaccine selection routine 274 coordinates with the patient eligibility determination routine 272 to identify vaccines which the patient is eligible to receive for use with the client application 266.

Preferably, a user such as a pharmacist may launch the client application 266 from a pharmacy workstation 128 to access the central processing system 140 to implement the vaccine administration system 100. In other embodiments, the client application 266 may be launched from a web-enabled device, such as one of the web-enabled devices 206-216. Additionally, the user may also launch or instantiate any other suitable user interface application (e.g., the native application or web browser 270, or any other one of the plurality of software applications 264) to access the central processing system 140, the facility servers 126, or the server applications 113 to realize the vaccine administration system 100.

As mentioned above, the term "pharmacist" may include technicians and other pharmacy personnel. Also, as used herein, the term "customer" indicates someone purchasing a retail product but may additionally be, by way of example, a patient (i.e., the person named on the prescription), a guardian (e.g., the parent of a child named on the prescription), a care-giver (i.e., anyone who takes care of a patient or picks up the medication on the patient's behalf), etc. Moreover, the term "customer" is not limited to a single person, but may instead be any person or persons having a reason or desire to purchase one or more retail products or to perform one or more functions relating to prescription medications, whether the prescriptions are related to a single patient or multiple patients. For example, a customer could be a caregiver responsible for patients with a specific disease that progresses in a known manner. The caregiver customer might greatly benefit from gaining information related to various medications and health products to assist in his or her caregiver responsibilities. In any event, while the term "customer" may be used interchangeably with the term "patient," in this specification the term "patient" is used primarily so as to avoid confusion.

Furthermore, the term "health care provider" as used herein, may refer to an individual or organization that provides preventative, curative, diagnostic, therapeutic, promotional, or rehabilitative health care services to patients. A health care provider may include, for example, a physician, physician assistant, nurse, pharmacist, etc. Generally, the term "user" is used when referring to a person who is operating one of the pharmacy workstations 128 or web-enabled devices 206-216 and is not exclusive of the terms "pharmacist," "health care provider," "customer," and "patient."

As described above, the database 146, illustrated in FIG. 1A, includes various information about the pharmacy's patients and vaccine eligibility requirements. Patient records are among the exemplary data that the vaccine administration system 100 may store on the database 146. A patient record contains important information about the patient and the various pharmacy services that have been invoked by, or on behalf of, the patient in a patient profile. The patient profile includes basic biographical information about the patient, such as a patient name, a patient address, a patient phone number, a patient birth date, patient prescription history, a default pickup store for the patient, patient insurance information, patient medical characteristics or a link to the patient's electronic medical records (EMR), etc. Vaccine eligibility requirements may also be stored on the database 146. Vaccine eligibility requirements may include, for each vaccine-preventable disease, a set of federal eligibility requirements, a set of state eligibility requirements for each state, whether each state allows high risk patients who are otherwise ineligible to receive the vaccines, a set of medical conditions used to characterize a patient as high risk for each state, etc.

As shown in FIG. 1B, to access the central processing system 140, the facility servers 126, or the server applications 113, the user executes the client application 266 on one of the pharmacy workstations 128, or in some embodiments, the web-enabled devices 206-216. Using the client application 266, the user may request server data (not shown) by navigating a series of client application screens. FIGS. 2A and 2C-2F depict client application pages or screens that the central processing system 140, the facility servers 126, or the server applications 113 may transmit in various embodiments of the vaccine administration system 100. However, the screens depicted in FIGS. 2A and 2C-2F are merely illustrations of an exemplary embodiment. In some embodiments, the central processing system 140 may transmit web pages.

In any event, the user may launch the client application 266 from one of the pharmacy workstations 128 via any suitable manner, such as touch-selecting a client application icon (not shown) on the display 240 of the pharmacy workstation or double-clicking on the client application icon via a mouse or a track pad. After the user launches the client application 266, a patient information retrieval screen of the client application 266 is displayed to the user on the pharmacy workstation 128. As mentioned above, the user may be a pharmacist.

With reference now to FIG. 2A, a patient information retrieval screen 300 of the client application 266 is displayed to the user on the pharmacy workstation 128. The patient information retrieval screen 300 may include a user control such as a drop down menu 314 for selecting a vaccine that the patient would like to receive 302. The drop menu 314 may allow the user to select a disease from several vaccine-preventable diseases. For example, the drop down menu 314 may allow the user to select from measles, cholera, meningitis, influenza, diphtheria, mumps, tetanus, hepatitis A, pertussis, tuberculosis, hepatitis B, pneumococcal disease, typhoid fever, hepatitis E, poliomyelitis, shingles, human papilloma-virus, yellow fever, etc. The patient information retrieval screen 300 may also include several user controls for entering patient biographical data. For example, the patient retrieval screen 300 may include a user control such as "Yes/No" radio buttons 316 for selecting whether the patient has a prescription for the requested vaccine. Further, the patient retrieval screen 300 may include user controls such as "Male/Female" radio buttons 318 for entering the patient's gender, a free form text field 320 for entering the patient's birth date, "Yes/No" radio buttons 322 for selecting whether the patient has had a severe reaction to any vaccine previously, and "Yes/No" radio buttons 324 for selecting whether the patient may be pregnant.

In some scenarios, the user may ask the patient each of the questions 302-312 on the patient retrieval screen 300 and may enter the patient's answers via the user controls 314-324. Each of the questions 302-312 may be used to determine whether the patient is eligible to receive vaccines for the vaccine-preventable disease selected using the drop down menu 314. Each of the answers may be transmitted to the central processing system 140 as patient biographical data.

In other scenarios, the client application 266 may communicate with the central processing system 140 to pre-fill the answers. For example, the client application 266 may communicate with the central processing system 140 to retrieve patient biographical data from the database 146, such as the patient's gender, date of birth, and medical characteristics. Additionally, the central processing system 140 may interface with the patient's EMR to retrieve medical characteristics for the patient, such as chronic health conditions, previous illnesses, vaccination records, etc., which may be communicated to the client application 266. The client application 266 may then identify answers to at least some of the questions 302-312 using the patient biographical data and/or medical characteristics and pre-fill these answers. For example, if the patient biographical data indicates that the patient is a female, the "Female" radio button 318 may automatically be selected. In another example, if the medical characteristics indicate the patient recently received a prescription for a vaccine, the "Yes" radio button 316 indicating that the patient has a prescription may automatically be selected. Then the user may ask the patient the questions which do not have pre-filled answers. In some scenarios, the user may continue to ask the patient the questions which have pre-filled answers to ensure that the pre-filled answers are up to date, such as whether the patient is pregnant.

While the user controls in the patient information retrieval screen 300 are shown as a drop down menu 314, radio buttons 316, 318, 322, and 324, and a free form text field 320, this is merely one example embodiment. It should be understood that the user controls may be displayed in any suitable manner. For example, the drop down menu 314 may be a free form text field, one or more radio buttons, one or more check boxes, or any combination of these. The "Yes/No" radio buttons 316 may be a drop down menu, a free form text field, one or more check boxes, etc.

In any event, the patient information retrieval screen 300 may also include a submit button 326 for transmitting the answers selected via the user controls 314-324 to the central processing system 140. For example, the central processing system 140 may receive indications that the patient requests a vaccine to prevent tuberculosis, the patient does not have a prescription, the patient is a female born on Feb. 3, 1999, the patient has not had a severe reaction to any vaccines, and the patient is not pregnant. In some embodiments, the central processing system 140 may compare the patient biographical data from the patient's answers to patient biographical data in the patient's profile. The patient's profile may be updated to include the patient biographical data from the patient's answers. For example, if the patient's profile indicates that the patient is not pregnant and the central processing system 140 receives an indication that the patient is pregnant, the patient's profile may be updated to indicate that she is pregnant.

In any event, upon receiving the answers, the central processing system 140 and more specifically, the software modules 171A and 171B may in turn, identify the specified vaccine-preventable disease and retrieve a set of eligibility requirements for the patient to receive the requested vaccine. The eligibility requirements may be retrieved from the database 146.

FIG. 2B illustrates an exemplary eligibility data table 350 which may be retrieved from the database 146 and which includes a set of eligibility requirements. The central processing server 140 may compare the set of eligibility requirements to the patient biographical data to assess the patient's eligibility to receive vaccines corresponding to a specified vaccine-preventable disease. For example, the eligibility data table 350 may include an indication of whether the requirements are federal or for a particular state 370, an indication of the vaccine-preventable disease 375, an indication of eligibility requirements to receive the vaccine 380, an indication of whether high risk patients can receive the vaccine when they do not otherwise meet the eligibility requirements 385, and indications of the criteria for characterizing a patient as high risk 390.

The central processing server 140 may identify the specified vaccine-preventable disease in the eligibility data table 350 and retrieve the set of eligibility requirements for the patient's state and the federal eligibility requirements. In some embodiments, the patient's state may be determined based on an indication of the state in which the pharmacy workstation 128 is located. For example, each pharmacy workstation 128 may store in the data storage 262 an indication of the state in which the pharmacy workstation 128 is located and transmit the indication of the state to the central processing system 140 along with the patient biographical data. In other embodiments, the database 146 may include an indication of the patient's state or the patient information retrieval screen 300 may include a user control for entering the patient's state.

In any event, if the patient is in Illinois and requests a vaccine to prevent pneumonia, for example, the central processing system 140 may retrieve an entry 356 which includes eligibility requirements 380 in Illinois for pneumonia vaccines. The central processing system 140 may also retrieve an entry 358 which includes federal eligibility requirements 380 for pneumonia vaccines. The eligibility requirements 380 may include an eligible age range for receiving the vaccines such as ages 0-5 and 65 and older for receiving pneumonia vaccines in Illinois as indicated in entry 356. The eligibility requirements 380 may also include contraindications to the vaccines such as an allergic reaction to a prior dose or allergies to components of the pneumonia vaccines. Additional contraindications for the pneumonia vaccines or vaccines to prevent other diseases may include pregnancy, severe immunodeficiency or HIV, encephalopathy, etc.

While the Illinois and federal eligibility requirements 380 in entries 356 and 358, respectively, may be the same, the Illinois eligibility requirements may contain additional or alternative requirements to the federal eligibility requirements. Accordingly, the central processing system 140 may compare the patient's biographical data to both the federal and state eligibility requirements to ensure that both sets of eligibility requirements are satisfied.

Additionally, in some embodiments, each pharmacy 112 may include pharmacy qualifications which may be used to determine whether the pharmacy is able to administer vaccines for the vaccine-preventable disease to the patient. For example, a pharmacy 112 may need to be certified to dispense yellow fever vaccines. If the pharmacy 112 is not certified, the patient may be ineligible to receive the vaccine from the pharmacy 112. In another example, some vaccines may need to be kept at certain temperatures, such as under 40 degrees. If the pharmacy 112 does not have a health care provider on site who can administer the vaccine and the pharmacy 112 does not have a mechanism for ensuring that the vaccine remains under 40 degrees until it reaches a health care provider, the patient may also be ineligible to receive the vaccine from the pharmacy 112. Pharmacy qualifications for each pharmacy may be included in the eligibility data table 350 or may be included in the data storage 262 of each pharmacy workstation 128 and transmitted to the central processing system 140.

If the Illinois patient is outside of the age range for receiving a pneumonia vaccine according to the Illinois and federal requirements (e.g., the patient is between the ages of 6 and 65) and does not have any contraindications to the pneumonia vaccines (e.g., the patient is not allergic to the vaccines or any of its components), the central processing system 140 may determine whether high risk patients are allowed to receive the vaccines according to state and federal law. The data entries 356 and 358 both indicate that high risk patients 385 are allowed to receive the pneumonia vaccines according to Illinois and federal law. However, the data entry 356 includes additional high risk criteria 390 which may be used to characterize a patient as high risk in Illinois when compared to the federal data entry 358. Accordingly, the central processing system 140 may determine that the patient is characterized as high risk if the patient has any of the medical conditions within either of data entry 356 or data entry 358 (e.g., any of sickle cell disease, HIV, lymphoma, Hodgkin disease, organ transplant, cirrhosis, and diabetes). In other embodiments, the patient may be characterized as high risk if the patient has some combination of the medical conditions included in the state or federal eligibility requirements for the specified vaccine-preventable disease.

In any event, the central processing system 140 may transmit the identified medical conditions which characterize the patient as high risk to the pharmacy workstation 128 to be displayed by the client application 266 as described in more detail below. The user may then select the medical conditions on the display which are associated with the patient.

While the eligibility data table 350 includes five data entries for three diseases, three states, and one federal, it should be understood that different numbers of data entries, diseases, states, and federal eligibility requirements may be utilized. For example, the eligibility data table 350 may include thousands of data entries for hundreds of diseases including sets of eligibility requirements for each disease in all 50 states and federal eligibility requirements for each disease. Additionally, the sets of eligibility requirements in the data entries and high risk criteria are merely example eligibility requirements and high risk criteria. Any suitable eligibility requirements and high risk criteria may be included which is in accordance with federal and state law.

FIG. 2C illustrates an exemplary additional health risk information retrieval screen 400 of the client application 266 which may be displayed to the user on the pharmacy workstation 128. For example, the additional health risk information retrieval screen 400 may be displayed when the patient does not meet the eligibility requirements for vaccines corresponding to a specified vaccine-preventable disease according to federal and state law, but federal and state law allow for high risk patients to receive the vaccines. In some embodiments, patients who have contraindications to the vaccines may not be able to receive any of the vaccines even if they are high risk.

Accordingly, the additional health risk information retrieval screen 400 may be displayed when the patient falls outside the age range of the eligibility requirements or fails to meet some other criteria within the eligibility requirements but does not have any contraindications to the vaccines. For example, according to the eligibility data table 350 as shown in FIG. 2B, a patient requesting a pneumonia vaccine may receive one of the pneumonia vaccines when the patient is between 6 and 65 years old, is not allergic to the pneumonia vaccine or one of its components, and is characterized as high risk.

The additional information health risk retrieval screen 400 may display indications of each of the medical conditions used to characterize the patient as high risk for a vaccine-preventable disease according to federal and state law. The displayed medical conditions may include a damaged spleen, alcoholism, asthma, brain or spinal cord fluid leaks, cardiac failure, chemotherapy, chronic kidney failure, chronic liver disease, chronic lung disease, cochlear implant, congenital heart disease, diabetes, hemoglobin disorder, HIV, Hodgkin disease, immune system disorder, immunosuppression therapy, kidney disease, leukemia, lymphomas, malignant cancer, multiple myeloma, sickle cell disease, and solid organ transplant. Medical conditions which may be used to characterize the patient as high risk for a vaccine-preventable disease may also include exposure to certain diseases. For example, working with Hepatitis A infected primates may be a medical condition used to characterize a patient as high risk for Hepatitis A. In another example, frequently travelling to regions with high infection rates of Hepatitis B may be a medical condition used to characterize a patient as high risk for Hepatitis B.

Moreover, the additional health risk information retrieval screen 400 may display indications of user controls, such as checkboxes 402-408 for selecting whether the patient has any of the displayed medical conditions. While the user controls in the additional health risk information retrieval screen 400 are shown as checkboxes 402-408, this is merely one example embodiment. It should be understood that the user controls may be displayed in any suitable manner. For example, each of the checkboxes 402-408 may be a free form text field, one or more radio buttons, a drop-down menu, or any combination of these. The additional health risk information retrieval screen 400 also includes a submit button 410, which when selected, may cause the pharmacy workstation 128 to transmit the selected medical conditions to the central processing server 140.

The medical conditions displayed on the additional health risk information retrieval screen 400 may be used to characterize the patient as high risk for a specific vaccine-preventable disease, such as pneumonia. However, the additional health risk information retrieval screen 400 may display any medical conditions for any vaccine-preventable disease. For example, if the patient requests a hepatitis A vaccine, the additional health risk information retrieval screen 400 may display indications of whether the patient is an injection drug user, whether the patient has chronic liver disease, whether the patient works with Hepatitis A infected primates, etc. In other embodiments, the additional health risk information retrieval screen 400 may not display medical conditions for a specific vaccine-preventable disease and may instead display any number of medical conditions which a patient may have.

The user may then select the medical characteristics associated with the patient and the selected medical characteristics may be compared to the medical conditions used to characterize the patient as high risk for the specified vaccine-preventable disease. Additionally, the selected medical characteristics may be compared to the medical characteristics in the patient's profile in the database 146. The patient's profile and EMR may be updated with selected medical characteristics which were not previously associated with the patient.

When the central processing system 140 identifies the patient as high risk for the vaccine-preventable disease or the patient meets the eligibility requirements, such as the eligibility requirements 380 in the eligibility data table 350 as shown in FIG. 2B, the central processing system 140 generates indications of several vaccines corresponding to the vaccine-preventable disease which may be administered to the patient. For example, if the vaccine-preventable disease is influenza, the vaccines may include a live attenuated influenza vaccine, an inactivated influenza vaccine, a quadrivalent influenza vaccine, an intradermal influenza vaccine, a recombinant trivalent influenza vaccine. An exemplary vaccination screen 420 of the client application 266 is shown in FIG. 2D, which may be displayed to the user on the pharmacy workstation 128. The vaccination screen 420 may include indications of the several vaccines corresponding to the vaccine-preventable disease which may be administered to the patient.

For example, the vaccination screen 420 may display Fluvirin® 5 milliliter (ml) multi-dose vial (MDV) trivalent influenza vaccine (TIV) 422, Fluvirin® 0.5 ml pre-filled syringe (PFS) TIV 424, Flumist® quadrivalent (QUAD) live attenuated intranasal spray 426, Fluzone® 0.5 ml MDV TIV 428, and Fluarix® 0.5 ml PFS QUAD 430. Each indication of a vaccine may be adjacent to a user control, such as a checkbox 432 for selecting the vaccine. The user may select the checkbox adjacent to a vaccine when the user wants the selected vaccine to be administered to the patient. For example, when the user selects checkbox 432, the central processing system 140 may generate a vaccination standing order for a health care provider to administer Fluvirin® 5 ml MDV TIV 422 to the patient, as described in more detail below.

In some embodiments, each vaccine-preventable disease may correspond to several types (e.g., quadrivalent, trivalent, syringe, nasal spray, etc.), brands (e.g., Fluvirin®, Flumist®, Fluzone®, Fluarix®, etc.), and/or dosages (e.g., 0.2 ml, 0.5 ml, 1 ml, 5 ml, etc.) of vaccines. For each vaccine corresponding to the vaccine-preventable disease, the central processing system 140 may obtain contraindications for the vaccine, an optimal age range for receiving the vaccine, precautions, etc. The contraindications, optimal age range, and precautions may be compared to the patient biographical data and medical characteristics for the patient, and if the patient is outside the optimal age range, has contraindications with the vaccine, or has medical characteristics indicated in the precautions, the vaccine may not be included in the vaccination screen 420.

For example, an egg allergy, immunodeficiency such as HIV, pregnancy, and being over 50 years old may be contraindications for the live attenuated intranasal spray influenza vaccine. Precautions for the live attenuated intranasal spray influenza vaccine 426 may include having a moderate or severe acute illness, asthma, chronic lung disease, diabetes, chronic kidney disease, neurological disease, and metabolic disorders. Contraindications for the Fluvirin® 5 ml MDV TIV 422 may include an egg allergy.

In some embodiments, each vaccine corresponding to the vaccine-preventable disease may be ranked and displayed in descending order with the highest ranking vaccine for the patient displayed at the top of the vaccination screen 420. In this embodiment, when the patient has medical characteristics indicated in the precautions for the vaccine, the vaccine may be displayed on the vaccination screen 420 but may be ranked lower than vaccines which do not have precautions matching with the patient's medical characteristics. Additionally, the vaccines may be ranked according to their side effects or lack thereof, according to their efficacies at clinical trials, according to the cost of the vaccines, etc., or a combination of these. For example, each vaccine which does not have precautions matching with the patient's medical characteristics may be ranked higher than each vaccine which has precautions matching with the patient's medical characteristics. Then each vaccine which does not have precautions matching with the patient's medical characteristics may be further ranked based on efficacy at clinical trials.

In some embodiments, each vaccine may be assigned a first score corresponding to the efficacy of the vaccine, a second score corresponding to the amount and/or severity of the side effects associated with the vaccine, and a third score corresponding to the cost of the vaccine. The scores may then be combined and/or aggregated in any suitable manner to generate an overall score for each vaccine, and the vaccines may be ranked based on their corresponding overall scores. For example, the overall score may be an average of the first, second, and third scores or a weighted average where the efficacy score is assigned the highest weight. In some embodiments, the highest ranking vaccine may include an indication on the vaccination screen 420 that the vaccine is "Preferred" 434. In any event, when the user selects a user control adjacent to one of the vaccines, such as the checkbox 432 adjacent to Fluvirin® 5 ml MDV TIV 422, the central processing system 140 may receive an indication of the selection and may generate a vaccination standing order for the health care provider to administer Fluvirin® 5 ml MDV TIV 422 to the patient.

FIG. 2E illustrates an exemplary ineligible vaccination screen 450 of the client application 266 when the patient is ineligible to receive vaccines for the vaccine-preventable disease, which may be displayed to the user on the pharmacy workstation 128. The vaccination screen 450 may include an indication that vaccines corresponding to the specified vaccine-preventable disease cannot be administered to the patient 452. The central processing system 140 may generate the ineligible vaccination screen 450 in several instances.

The ineligible vaccination screen 450 may be generated when the patient does not meet the eligibility requirements according to federal and state law for the patient's state and federal or state law does not allow high risk patients to receive vaccines for the vaccine-preventable disease. Furthermore, the ineligible vaccination screen 450 may be generated when the patient does not meet the eligibility requirements and the patient is not characterized as high risk according to federal and state law for the patient's state. The ineligible vaccination screen 450 may also be generated when the patient meets the eligibility requirements or is characterized as high risk but based on pharmacy qualifications the pharmacy 112 is unable to dispense vaccines for the vaccine-preventable disease.

For example, a pharmacy 112 may need to be certified to dispense a yellow fever vaccine. If the pharmacy 112 is not certified, the client application 266 may display the ineligible vaccination screen 450. In another example, some vaccines may need to be kept at certain temperatures, such as under 40 degrees. If the pharmacy 112 does not have a health care provider on site who can administer the vaccine and the pharmacy 112 does not have a mechanism for ensuring that the vaccine remains under 40 degrees until it reaches a health care provider, the client application 266 may display the ineligible vaccination screen 450. In some embodiments, the pharmacy workstation 128 may store indications of vaccines which the pharmacy 112 is unable to dispense and/or indications of other pharmacy qualifications. For example, the indications may be stored in the data storage 262.

When the patient is eligible to receive vaccines for the specified vaccine-preventable disease and the user selects one of the vaccines from the vaccination screen 420 as shown in FIG. 2D, the central processing system 140 may generate a vaccination standing order. The vaccination standing order may be displayed to the user on the pharmacy workstation 128 via a vaccination standing order screen 460 of the client application 266 as shown in FIG. 2F.

FIG. 2F illustrates an exemplary vaccination standing order screen 460 which may include an indication of the patient's name 462, date of birth 464, and age 466. The vaccination standing order screen 460 may also include an indication of the vaccine to be administered 468, such as Fluvirin® 5 ml MDV TIV, a national drug code (NDC) number 470 which may be a unique identifier for the vaccine, a quantity for the vaccine 472, and directions for administering the vaccine 474 such as, "Shake vigorously and administer 0.5 ml." In some embodiments, the vaccination standing order screen 460 may include more detailed directions such as, "Prior to vaccinating, the vial should be shaken vigorously. Inspect the vial for discoloration and particulate matter. Then insert syringe with needle into vial and draw 0.5 ml. Administer a single 0.5 ml injection into the deltoid muscle."

The exemplary vaccination standing order screen 460 may also include the name of the administering pharmacist 476 or other health care provider, a drug enforcement agency (DEA) or national provider identifier (NPI) number 478 uniquely identifying the health care provider, and a phone number 480 for the health care provider. In some embodiments, the pharmacy workstation 128 may store and transmit an indication of the administering pharmacist to the central processing system 140 which may include the indication on the vaccination standing order screen 460. The pharmacy workstation 128 may store indications of the administering pharmacist on site at different dates and times. In other embodiments, the vaccination standing order screen 460 may include user controls such as a free form text field for entering the administering pharmacist or other health care provider information. When the vaccination cannot be administered by a pharmacist, the central processing system may retrieve an indication of the patient's physician for example, from the patient's EMR and may include the indication of the patient's physician on the vaccination standing order screen 460. In any event, the user may verify that the information on the vaccination standing order screen 460 is correct and the vaccination standing order may be provided to the pharmacist or other health care provider, such as the patient's physician for administering the vaccination 468. Additionally, the vaccination standing order screen 460 may include an indication of whether the patient is characterized as high risk of contracting, being infected with, or suffering complications from, the specified vaccine-preventable disease.

In some embodiments, the central processing system 140 may also generate a vaccination information statement (VIS) explaining the vaccine-preventable disease corresponding to the vaccine, the benefits and risks of the vaccine, contraindications to the vaccine, symptoms of a severe reaction to the vaccine, etc. The VIS may be provided to the patient before the vaccine is administered.

Additionally, once the vaccine is administered to the patient, the central processing system 140 may generate a vaccination administration record (VAR). For example, the user may select a user control indicating that the vaccine has been administered which may be transmitted to the central processing system 140. The central processing system 140 may then generate a VAR which may include patient biographical data for the patient, such as the patient's name, date of birth, age, gender, address, primary physician, etc. The VAR may also include an indication of whether the patient is characterized as high risk for the vaccine-preventable disease according to federal and state law, an indication of the administered vaccine, an NDC number for the administered vaccine, a dosage for the administered vaccine, a date on which the vaccine was administered, and an indication of the health care provider who administered the vaccine. In some embodiments, the VAR may be transmitted to the patient's EMR or included in the patient's profile in the database 146 to update the patient's records.

Figure 3:
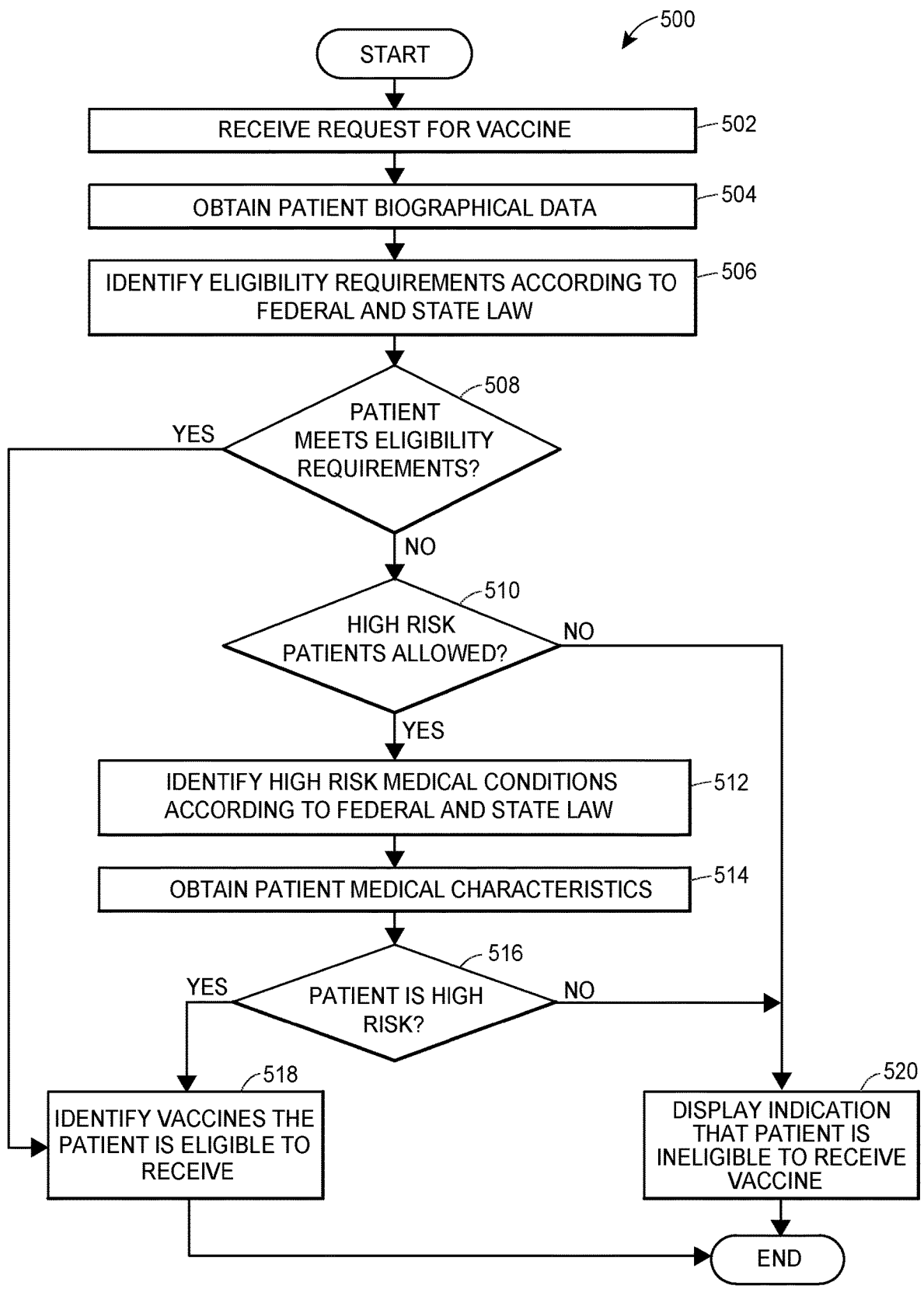
FIG. 3 illustrates a flow diagram representing an exemplary method for identifying vaccines to be administered to a patient in accordance with the presently described embodiments.

FIG. 3 depicts a flow diagram of an exemplary method 500 for identifying vaccines to be administered to a patient. The method 500 may be executed on the central processing system 140. In some embodiments, the method 500 may be implemented in a set of instructions stored on a non-transitory computer-readable memory and executable on one or more processors of the central processing system. For example, the method 500 may be performed by the software modules 171A and 171B as shown in FIG. 1. In other embodiments, the method 500 may be implemented by a facility server 126 or a combination of these devices.

At block 502, the central processing system 140 may receive a request from a patient to receive a vaccine for a specified vaccine-preventable disease. For example, the central processing system 140 may receive a selection from the patient information retrieval screen 300 as shown in FIG. 2A indicating that the patient would like to receive a vaccine for measles, cholera, meningitis, influenza, diphtheria, mumps, tetanus, hepatitis A, pertussis, tuberculosis, hepatitis B, pneumonia, typhoid fever, hepatitis E, poliomyelitis, shingles, human papilloma-virus, yellow fever, etc. The central processing system 140 may also obtain patient biographical data for the patient (block 504). The patient biographical data may be obtained from the patient information retrieval screen 300 or may be obtained from the patient's profile in the database 146 and/or the patient's EMR.

Additionally, the central processing system 140 may identify eligibility requirements for receiving vaccines for the specified vaccine-preventable disease according to federal and state law for the patient's state (block 506). In some embodiments, the patient's state may be determined based on an indication of the state in which the pharmacy workstation 128 is located. In other embodiments, the database 146 may include an indication of the patient's state. The eligibility requirements may be compared to the patient's biographical data to determine whether the patient is eligible to receive the vaccine (block 508). For example, the eligibility requirements may specify that eligible patients may be between ages 10 and 25 who are not pregnant and have not had an allergic reaction to a prior does of the vaccine.

If the patient meets the eligibility requirements, the central processing system 140 may identify several vaccines corresponding to the vaccine-preventable disease that the patient is eligible to receive (block 518). For example, the vaccines may include a live attenuated influenza vaccine, an inactivated influenza vaccine, a quadrivalent influenza vaccine, an intradermal influenza vaccine, a recombinant trivalent influenza vaccine, etc. The central processing system 140 may transmit indications of the identified vaccines to the client application 266 to be displayed on the pharmacy workstation. In some embodiments, the vaccines may be displayed in a ranked order according to side effects, efficacy, cost, etc.

On the other hand, if the patient does not meet the eligibility requirements, the central processing system 140 may determine whether high risk patients who are not otherwise eligible are allowed to receive vaccines for the vaccine-preventable disease (block 510). In some embodiments, patients who have contraindications to vaccines for the vaccine-preventable disease may not be able to receive any of the vaccines even if they may be characterized as high risk. In any event, if high risk patients are not allowed to receive vaccines, the central processing system 140 may generate an indication that the patient is ineligible to receive vaccines for the specified vaccine-preventable disease (block 520). If high risk patients are allowed to receive vaccines, the central processing system 140 may identify medical conditions which may be used to characterize the patient as high risk according to federal and state law for the patient's state. For example, for pneumonia, patients having any of sickle cell disease, HIV, lymphoma, Hodgkin disease, organ transplant, cirrhosis, or diabetes may be characterized as high risk.

The central processing system 140 may also obtain medical characteristics for the patient (block 514). For example, the medical characteristics may be obtained from the additional health risk information retrieval screen 400 or may be obtained from the patient's profile in the database 146 and/or the patient's EMR. The patient's medical characteristics may be compared to the medical conditions used to characterize the patient as high risk (block 516), and if the patient is characterized as high risk, the central processing system 140 may identify several vaccines corresponding to the vaccine-preventable disease that the patient is eligible to receive (block 518). On the other hand, if the patient is not characterized as high risk, the central processing system 140 may generate an indication that the patient is ineligible to receive vaccines for the specified vaccine-preventable disease (block 520). For example, the central processing system 140 may cause the client application 266 to display the ineligible vaccination screen 450 as shown in FIG. 2E on the pharmacy workstation.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Additionally, certain embodiments are described herein as including logic or a number of routines, subroutines, applications, or instructions. These may constitute either software (e.g., code embodied on a machine-readable medium or in a transmission signal) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of locations.

The performance of certain of the operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description, and the claims that follow, should be read to include one or at least one and the singular also includes the plural unless it is obvious that it is meant otherwise.

This detailed description is to be construed as exemplary only and does not describe every possible embodiment, as describing every possible embodiment would be impractical, if not impossible. One could implement numerous alternate embodiments, using either current technology or technology developed after the filing date of this application.

We claim:

1. A computer-implemented method for identifying vaccines to be administered to a patient, the method executed by one or more processors programmed to perform the method, the method comprising:

receiving, at one or more processors, a request for a vaccine for preventing a specified disease to be administered to a patient;

obtaining, by the one or more processors, patient biographical data for the patient;

identifying, by the one or more processors, a set of eligibility requirements for the patient to receive vaccines for preventing the specified disease according to federal and state law based on a location of the patient, the set of eligibility requirements including contraindications for the vaccines;

determining, by the one or more processors, whether the patient meets the set of eligibility requirements by comparing the set of patient eligibility requirements to the patient biographical data;

determining, by the one or more processors, that the patient does not meet the set of eligibility requirements;

determining, by the one or more processors, that patients who do not meet the set of eligibility requirements and who have high risk medial conditions qualify to receive the vaccines for preventing the specified disease according to the state and federal law;

obtaining, by the one or more processors, medical characteristics for the patient;

identifying, by the one or more processors, a set of high risk medical conditions associated with the vaccines for preventing the specified disease according to the federal and state law;

determining, by the one or more processors, whether the patient is high risk by comparing the set of high risk medical conditions to the medical characteristics for the patient; and when the patient is high risk:

overriding the eligibility determination and identifying, by the one or more processors, a plurality of vaccines that the patient is eligible to receive based on the patient biographical data and the medical characteristics for the patient, wherein each of the plurality of vaccines prevent a same specified disease;

causing, by the one or more processors, indications of the plurality of vaccines to be displayed in a ranked order on a user interface for administering one of the plurality of vaccines to the patient, wherein each of the plurality of vaccines is ranked based on one or more of: an efficacy of the vaccine, an amount or severity of side effects associated with the vaccine, or a cost of the vaccine;

for a selected vaccine of the plurality of vaccines, causing, by the one or more processors, a vaccination standing order to be pre-populated for the patient; and vaccinating the patient with the selected vaccine, wherein the pre-populated vaccination standing order is provided to a health care provider.

2. The method of claim 1, further comprising:
when the patient is high risk, causing, by the one or more processors, the vaccination standing order to be pre-populated with an indication that that patient has been identified as a high risk of being infected with, or suffering complications from, the specified disease.

3. The method of claim 1, further comprising:
causing, by the one or more processors, a patient information screen to be displayed on the user interface including one or more user controls for a user to enter patient biographical data for the patient; and
when the patient does not meet the set of eligibility requirements and the federal and state law allows for patients who have high risk medical conditions to receive vaccines for preventing the specified disease:
causing, by the one or more processors, an additional health risk information screen to be displayed on the user interface including one or more user controls for the user to enter the medical characteristics for the patient.

4. The method of claim 3, further comprising:
obtaining, by the one or more processors, a patient profile for the patient including indications of one or more medical characteristics corresponding to the patient;
comparing, by the one or more processors, the medical characteristics entered via the one or more user controls on the additional health risk information screen to the one or more medical characteristics in the patient profile; and
updating, by the one or more processors, the patient profile to include at least one medical characteristic entered via the one or more user controls which is not included in the one or more medical characteristics in the patient profile.

5. The method of claim 4, further comprising:
generating, by the one or more processors, a vaccination administration record (VAR) for the selected vaccine including a name of the selected vaccine, a date on which the vaccine was administered, a name and birthdate of the patient, and an indication of whether the patient is high risk;
updating, by the one or more processors, the patient profile to include the VAR.

6. The method of claim 1, further comprising:
causing, by the one or more processors, a vaccination information statement (VIS) for the selected vaccine to be displayed on the user interface.

7. The method of claim 1, further comprising:
selecting, by the one or more processors, the highest ranking vaccine of the plurality of vaccines.

8. The method of claim 1, wherein the patient biographical data includes a patient name, a patient birthdate, a patient gender, whether the patient experienced any adverse reactions to previous vaccines, and whether the patient is pregnant.

9. The method of claim 1, further comprising:
determining, by the one or more processors, whether the patient has a contraindication to the vaccines for preventing the specified disease based on the patient biographical data;
when the patient has a contraindication to the vaccines for preventing the specified disease, causing, by the one or more processors, an indication that the patient is ineligible to receive vaccines for preventing the vaccine-preventable disease to be displayed on the user interface.

10. A system for identifying vaccines to be administered to a patient, the system comprising:
one or more processors;
a communication network;
a non-transitory computer-readable memory coupled to the one or more processors, and the communication network, and storing thereon instructions that, when executed by the one or more processors, cause the system to:
receive, via the communication network, a request for a vaccine for preventing a specified disease to be administered to a patient;
obtain patient biographical data for the patient;
identify a set of eligibility requirements for the patient to receive vaccines for preventing the specified disease according to federal and state law based on a location of the patient, the set of eligibility requirements including contraindications for the vaccines;
determine whether the patient meets the set of eligibility requirements by comparing the set of patient eligibility requirements to the patient biographical data;
determine that the patient does not meet the set of eligibility requirements;
determine that patients who do not meet the set of eligibility requirements and who have high risk medial conditions qualify to receive the vaccines for preventing the specified disease according to the state and federal law;
obtain medical characteristics for the patient;
identify a set of high risk medical conditions associated with the vaccines for preventing the specified disease according to the federal and state law;
determine whether the patient is high risk by comparing the set of high risk medical conditions to the medical characteristics for the patient; and
when the patient is high risk:
override the eligibility determination and identify a plurality of vaccines that the patient is eligible to receive based on the patient biographical data and the medical characteristics for the patient, wherein each of the plurality of vaccines prevent a same specified disease;
cause, via the communication network, indications of the plurality of vaccines to be displayed in a ranked order on a user interface for administering one of the plurality of vaccines to the patient, wherein each of the plurality of vaccines is ranked based on one or more of: an efficacy of the vaccine, an amount or severity of side effects associated with the vaccine, or a cost of the vaccine;
for a selected vaccine of the plurality of vaccines, cause a vaccination standing order to be pre-populated for the patient;

wherein the pre-populated vaccination standing order is provided to a health care provider so as to cause the selected vaccine to be administered to the patient.

11. The system of claim 10, wherein the instructions further cause the system to:
when the patient is high risk, cause the vaccination standing order to be pre-populated with an indication that that patient has been identified as a high risk of being infected with, or suffering complications from, the specified disease.

12. The system of claim 10, wherein the instructions further cause the system to:
cause, via the communication network, a patient information screen to be displayed on the user interface including one or more user controls for a user to enter patient biographical data for the patient; and
when the patient does not meet the set of eligibility requirements and the federal and state law allows for patients who have high risk medical conditions to receive vaccines for preventing the specified disease:
cause, via the communication network, an additional health risk information screen to be displayed on the user interface including one or more user controls for the user to enter the medical characteristics for the patient.

13. The system of claim 12, wherein the instructions further cause the system to:
obtain a patient profile for the patient including indications of one or more medical characteristics corresponding to the patient;
compare the medical characteristics entered via the one or more user controls on the additional health risk information screen to the one or more medical characteristics in the patient profile; and
update the patient profile to include at least one medical characteristic entered via the one or more user controls which is not included in the one or more medical characteristics in the patient profile.

14. The system of claim 13, wherein the instructions further cause the system to:
generate a vaccination administration record (VAR) for the selected vaccine including a name of the selected vaccine, a date on which the vaccine was administered, a name and birthdate of the patient, and an indication of whether the patient is high risk; and
update the patient profile to include the VAR.

15. The system of claim 10, wherein the instructions further cause the system to:
cause, via the communication network, a vaccination information statement (VIS) for the selected vaccine to be displayed on the user interface.

16. The system of claim 10, wherein the instructions further cause the system to:
select the highest ranking vaccine of the plurality of vaccines.

17. The system of claim 10, wherein the patient biographical data includes a patient name, a patient birthdate, a patient gender, whether the patient experienced any adverse reactions to previous vaccines, and whether the patient is pregnant.

18. The system of claim 10, wherein the instructions further cause the system to:
determine whether the patient has a contraindication to the vaccines for preventing the specified disease based on the patient biographical data; and
when the patient has a contraindication to the vaccines for preventing the specified disease, cause an indication that the patient is ineligible to receive vaccines for preventing the vaccine-preventable disease to be displayed on the user interface.

* * * * *